United States Patent [19]
Bean et al.

[11] 3,975,238
[45] Aug. 17, 1976

[54] METHOD AND APPARATUS FOR DETECTING MOLECULES IN SOLUTIONS

[75] Inventors: Charles P. Bean; Ivar Giaever, both of Schenectady, N.Y.

[73] Assignee: General Electric Company, Schenectady, N.Y.

[22] Filed: June 26, 1975

[21] Appl. No.: 590,419

[52] U.S. Cl. .................... 195/103.5 R; 23/230 B; 23/253 R; 195/127; 204/195 B; 204/1 T; 424/12
[51] Int. Cl.² ................ G01N 21/10; G01N 33/16
[58] Field of Search .................. 23/230 B, 253 R; 424/12; 204/1 E, 195 B; 195/103.5 R, 127

[56] References Cited
UNITED STATES PATENTS

| | | | |
|---|---|---|---|
| 2,666,355 | 1/1954 | Trurnit | 424/12 X |
| 3,506,544 | 4/1970 | Silverman | 204/1 E |
| 3,838,011 | 9/1974 | Hagen | 194/103.5 R |
| 3,853,467 | 12/1974 | Giaever | 23/230 B |
| 3,880,524 | 4/1975 | Dill | 356/118 |
| 3,881,992 | 5/1975 | Ralston | 195/103.5 R |
| 3,896,008 | 7/1975 | Keyes | 204/1 E |

OTHER PUBLICATIONS

Chemical Abstracts, 80: 66002k (1974).
Chemical Abstracts, 81: 143618r (1974).
K. Dodgson et al., Comprehensive Biochemistry, 12, 103, Florkin & Stotz, eds., Elsevier, 1964.
I. Giaever, J. Immunol., 110, 1424 (1973).
E. E. Uzgiris et al., Rev. Sci. Instrum., 45, 120 (1974).
Chemical Abstracts, 78: 39972d (1973).

*Primary Examiner*—Morris O. Wolk
*Assistant Examiner*—Sidney Marantz
*Attorney, Agent, or Firm*—Marvin Snyder; Joseph T. Cohen; Jerome C. Squillaro

[57] ABSTRACT

A method and apparatus for optically detecting complexing of molecules in solution with surface-bound enzymes comprises slowly varying, in periodic fashion, the surface electrical potential so as to vary correspondingly the pH of the solution at the enzymatic sites through a range in which the Michaelis constant exhibits a relatively large change with pH variation. The potential is also oscillated over a smaller voltage range at a higher frequency. Phase sensitive detection of the output signal of an ellipsometer directed onto the surface provides a signal proportional to the concentration of complexing molecules.

15 Claims, 4 Drawing Figures

METHOD AND APPARATUS FOR DETECTING MOLECULES IN SOLUTIONS

INTRODUCTION

This invention relates to a method and apparatus for identifying and measuring molecules in solution, and more particularly to optically detecting bonding or complexing of molecules with surface-bound enzymes.

Enzymes are considered to be biological catalysts that can initiate and promote various chemical reactions in quite specific ways. They are not consumed in the reaction nor do they become part of the product formed by the reaction. Enzymes may be synthesized by plants, animals, viruses or microorganisms, and uniformly they are proteins. Enzyme-catalyzed reactions may be used for obtaining qualitative and quantitative information concerning substrates and the enzymes themselves.

The enzymatic reaction may be depicted as

Enzyme + Substrate $\underset{k_1}{\overset{k_2}{\rightleftarrows}}$ Complex $\overset{k_3}{\longrightarrow}$ Product + Enzyme where the end result is to aid the kinetics of the substrate (or substance acted upon by the enzyme), through the intermediate complexed enzyme or "complex" stage, to product reaction. It is known that sensitivity of enzymes to various substrates depends on the specific substrate since the fraction of complexed enzyme or intermediate substance varies with the specific substrate. Thus if the complexing can be detected, it can serve as a sensitive criterion and measure for the substrate. The present invention makes use of this fact.

It is also known that the Michaelis constant, $K_m$, is a function of acidity of the solution. The Michaelis constant is defined as the ratio $$\frac{k_1 + k_3}{k_2},$$

where $k_1$, $k_2$ and $k_3$ are the rate constants of the enzymatic reaction. In some solutions, a variation of 0.5 in pH can cause a variation of about 0.5 in $pK_m$ (or log $(1/K_m)$), which means that $K_m$ changes by more than a factor of 3 for this relatively minor change of pH. The present invention utilizes this fact to obtain increased sensitivity and easy readout of a signal proportional to the concentration of bonding molecules.

Local acidity of a solution near an electrode of irreversible polarity may be varied by establishing an electrical potential between the irreversible electrode and a reversible electrode. If this potential is $\Delta V$, then the pH is changed by $(\Delta V/59$ millivolts) pH units. The distance into the solution that this change will extend depends on the ionic concentration of the solution. For a one-thousandth normal solution of a simple salt, this distance is about 100 Angstroms.

By employing an ellipsometer to measure, optically, reflection and absorption of polarized light from a surface to infer presence of very thin surface films based upon changes in reflection and absorption of polarized light, complexing of molecules in question with surface-bound enzymes may be readily detected.

Accordingly, one object of the invention is to provide a method and apparatus for detecting complexing of molecules in solution with surface-bound enzymes in an enzymatic reaction.

Another object is to provide a method and apparatus for optically measuring concentration of substrate in an enzymatic reaction.

Another object is to provide a method and apparatus for optically measuring concentration of each of a plurality of substrates in a common solution reacting with each of a plurality of enzymes, respectively, in an enzymatic reaction.

Briefly, in accordance with a preferred embodiment of the invention, apparatus for detecting complexing of substrate molecules with surface-bound enzyme molecules in an enzymatic reaction comprises a bath of the substrate molecules in solution, a first electrode coated with a monomolecular layer of the enzyme molecules and situated within the bath, and a second electrode situated in the bath apart from the first electrode. Apparatus for producing a D.C. potential with a sinusoidal voltage superimposed thereon is coupled across the first and second electrodes. An ellipsometer is provided for analyzing polarized light reflected from the first electrode and producing an output signal having parameters which provide information concerning the nature of molecules on the first electrode.

In accordance with another embodiment of the invention, detection of complexing of substrate molecules with surface-bound enzyme molecules in an enzymatic reaction comprises immersing a first electrode coated with a monomolecular layer of the enzyme molecules in a bath of the substrate molecules in solution, immersing a second electrode in the bath, applying a sinusoidally-varying potential impressed on a D.C. potential across the first and second electrodes, and sensing changes in amount of polarized light reflected from the electrode to provide an indication of the complexing.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawings in which:

DESCRIPTION OF TYPICAL EMBODIMENTS

Figure 1:
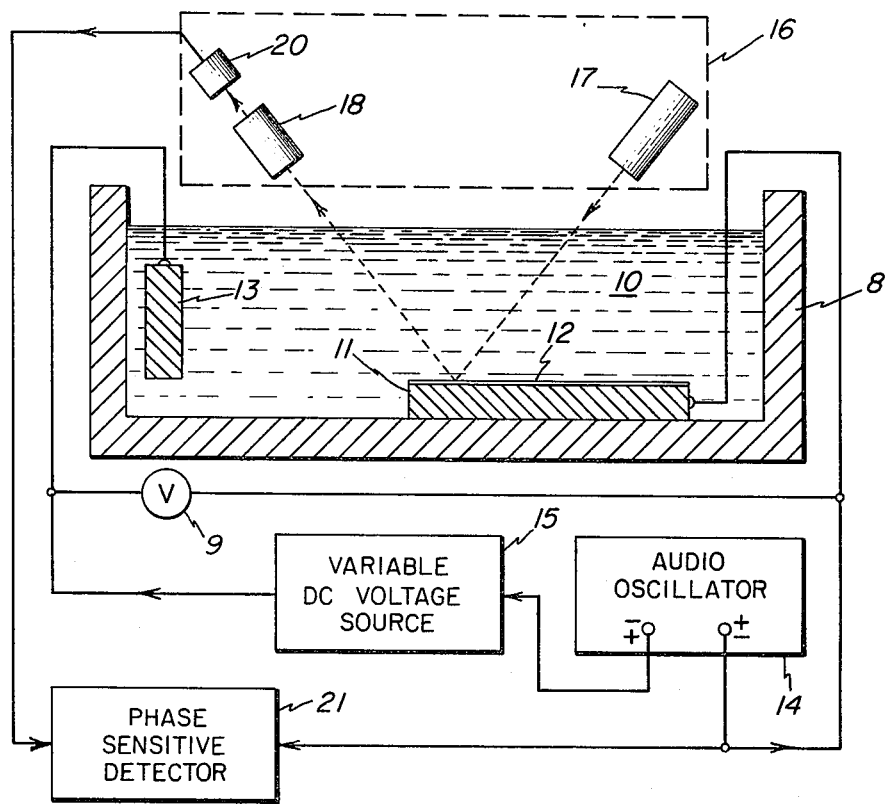
FIG. 1 is a schematic diagram of a preferred embodiment of the invention.

Enzymes, which uniformly are proteins, will adhere to a metallic surface in a monomolecular layer only, as noted in I. Giaever U.S. Pat. No. 3,853,467, issued Dec. 10, 1974 and assigned to the instant assignee. Thus in FIG. 1, apparatus employed to practice the instant invention is illustrated as including a tank 8 containing a bath 10 of a substrate solution to be analyzed, in which a pair of electrodes 11 and 13 are immersed. Irreversible electrode 11, which may typically be comprised of platinum or other noble metal, is coated with a monomolecular layer 12 of an appropriate enzyme. This coating is acquired by having previously immersed electrode 11 in a solution of the enzyme or enzymes to undergo the reaction to be studied, causing the electrode surface to adsorb a monomolecular layer of the enzyme or enzymes. Electrode 13, which may typically be comprised of platinum (although a reversible electrode of silver-silver chloride would also suffice), is immersed uncoated in bath 10.

Figure 2:
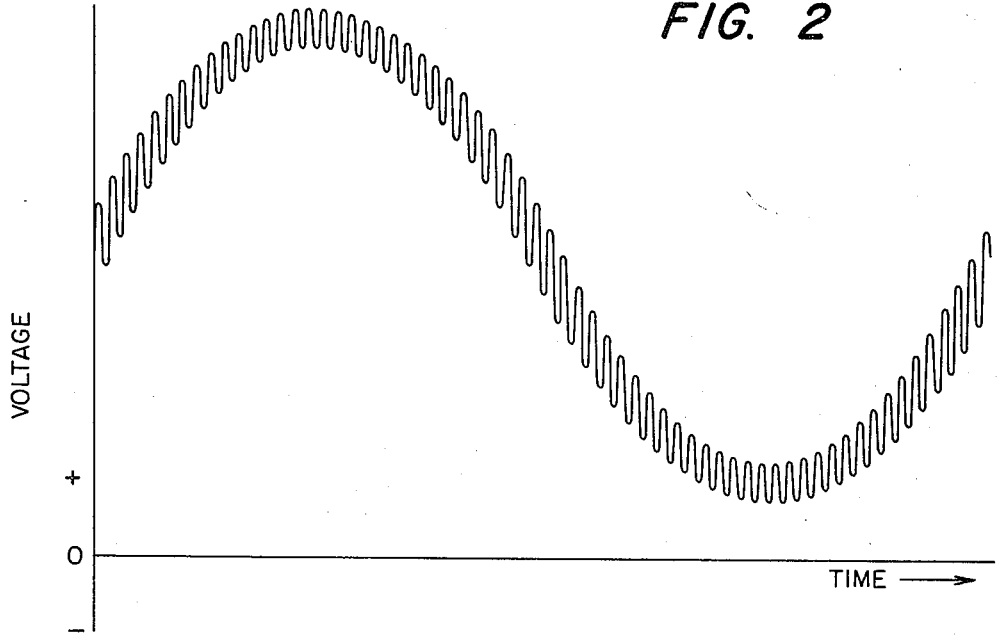
FIG. 2 is an illustration of a typical voltage waveform applied across the electrodes of the apparatus shown in FIG. 1.

An audio oscillator 14 and a D.C. voltage source 15 connected in series therewith furnish electrodes 11 and 13 with a potential difference, which may be monitored on a voltmeter 9 connected across electrodes 11 and 13. The amplitude of D.C. voltage source 15 may be varied very slowly in periodic fashion, such as over a 1-minute period, through its voltage range which, at its minimum value, exceeds the maximum voltage amplitude of audio oscillator 14. In addition, the potential difference on electrodes 11 and 13 is varied by oscillator 14 at a higher frequency such as 10 Hz., which is still low enough to accommodate the kinetics of the enzyme-substrate reaction. The potential difference across electrodes 11 and 13 thus constitutes a sinusoidally-varying potential of slowly-varying average amplitude, such as illustrated in FIG. 2.

As shown in FIG. 1, an ellipsometer 16 is employed to detect changes in thickness of layer 12 on electrode 11. An incident beam of polarized light is directed by output optical system 17 of ellipsometer 16 onto layer 12, and the reflected beam entering the ellipsometer is directed by input optical system 18 onto photodetector 20. A corresponding output signal generated by photodetector 20 is furnished to one input of a phase detector 21. The other input of phase detector 21 is connected to an output terminal of oscillator 14, which provides detector 21 with a standard for phase comparison.

In operation, layer 12 initially comprises a monomolecular layer of an enzyme such as saccharase, for example. This enzyme promotes splitting and hydrolysis of sugars, especially sucrose. Hence if the total number of saccharase-sucrose complexes is denoted by $N_c$ and the total number of enzymes (complexed and free) by $N_e$, then, in steady state with a free concentration of sucrose $N_s$, $$\frac{N_c}{N_e} = \frac{N_s}{(K_m + N_s)}$$

where $$K_m = \frac{(k_1 + k_3)}{k_2}$$

$k_1$, $k_2$ and $k_3$ being the rate constants of the enzymatic reaction

Enzyme + Substrate $\underset{k_1}{\overset{k_2}{\rightleftarrows}}$ Complex $\overset{k_3}{\longrightarrow}$ Product + Enzyme.

As the potential on electrode 11 is swept very slowly over its permitted range of approximately 500 to 1,000 millivolts, as by slowly varying output voltage of D.C. voltage source 15, the local pH at the enzymatic sites on the electrode is slowly changed. If the slow potential swing between electrodes 11 and 13 is 200 millivolts, then the pH is locally changed at the enzymatic sites on electrode 11 by (200/59 millivolts) pH units, or more than 3 pH units. By additionally oscillating this slowly-varying potential over a smaller voltage range of, for example, 10 millivolts, at a higher frequency which could be, for example, 10 Hertz, and if the average pH is in the region where $K_m$ changes, then the number of saccharase-sucrose complexes will oscillate with time.

The reactions of each of a sucrose substrate and a raffinose substrate with the enzyme saccharase of layer 12 result in the following Michaelis constant values:

| Enzyme | Substrate | $K_m$ (moles/liter) |
|---|---|---|
| Saccharase | Sucrose | $2.8 \times 10^{-2}$ |
| Saccharase | Raffinose | $4.5 \times 10^{-1}$ |

Saccharase is thus roughly 16 times more sensitive to the disaccharide sucrose than to the closely-related trisaccharide raffinose in that, for given low concentrations of substrate, the fraction of complex enzyme would be 16 times higher for the sucrose. Other unrelated molecules are not bound at all to the saccharase. Thus detection of the complexing can provide a sensitive criterion and measure for sucrose.

Figure 3:
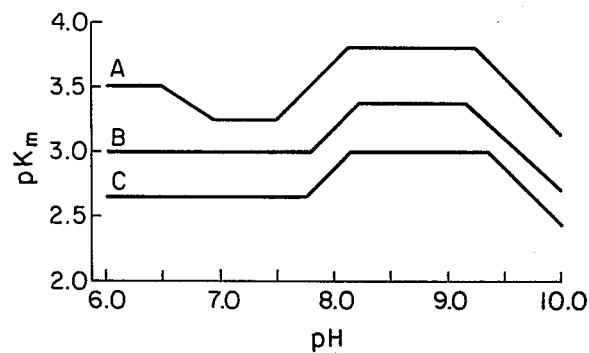
FIG. 3 is an illustration of variation in $pK_m$ with pH for reaction of the arylsulphatase of Alcaligenes metalcaligenes with various substrates.

FIG. 3 is a plot of several curves showing variation of $pK_m$ with pH for the enzyme arylsulphatase of Alcaligenes metalcaligenes, as set forth by K. Dodgson et al., *Biochemical Journal* 61 (1955) 374 and reproduced in Vol. 12 of *Comprehensive Biochemistry* edited by Florkin and Stotz, Elsevier Publishing Company (New York, 1964), at page 103. The substrates are A, nitrocatechol sulphate; B, p-nitrophenyl sulphate; and C, p-acetylphenyl sulphate. For each of the substrates, average pH changes, for example, at values of 8.0 and 9.7, and hence cyclical variation in pH about either of these values causes a correspondingly cyclical variation in number of complexes. Since the Michaelis constant is a function of acidity of the solution, it can be seen that $pK_m$ varies by about 0.5 for 0.5 variation in pH near either the 8.0 or 9.7 pH value. This means that $K_m$ changes by more than a factor of three for this relatively minor change of pH.

Figure 4:
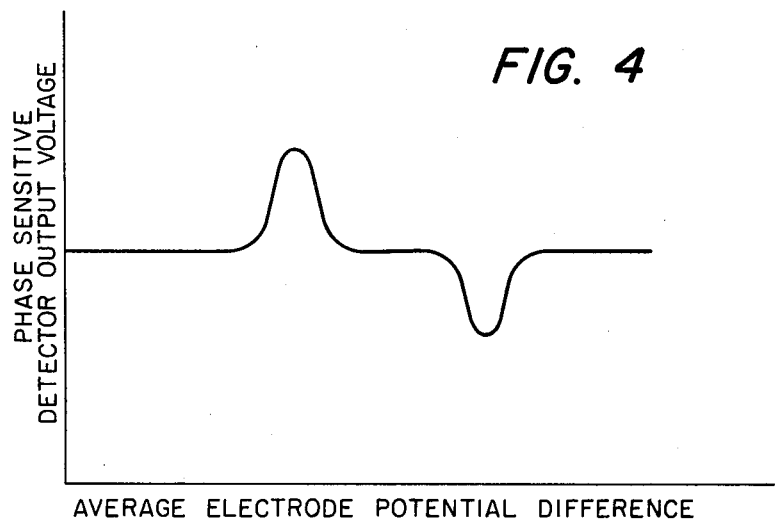
FIG. 4 is an illustration of a signal produced by the ellipsometer employed in the embodiment of FIG. 1.

Ellipsometer 16 of FIG. 1 measures reflection and absorption of polarized light by thin layer 12. From changes in these quantities, presence of very thin surface films can be inferred. When average pH is in the region where $K_m$ changes with changes in pH, as determined by amplitude of output voltage produced by D.C. voltage source 15, the number of complexes on electrode 11 oscillates with time according to the sinusoidal oscillation of voltage supplied by audio oscillator 14 and, accordingly, the output signal of photodetector 20 has a corresponding sinusoidal variation. Normally the sinusoidal variation in photodetector output signal would be unobservable, but by employing phase-sensitive detection, cancellation of noise voltages emanating from the audio oscillator circuit and determination of photodetector output voltage at a fixed phase relation to the voltage supplied by audio oscillator 14 allow this signal to be detected. The waveform of the detected signal is illustrated in FIG. 4. Moreover, if the concentration of substrate $N_s$ is very small with respect to the Michaelis constant $K_m$, the height of the peaks in the waveform of FIG. 4 will be proportional to the concentration of substrate, while the position of the peaks is characteristic of the particular enzyme and the pH of the bath. Thus if more than one type of enzyme is coated on electrode 11, the output voltage waveform produced by phase sensitive detector 21 would contain a series of identifiable peaks. This provides the capacity to analyze the solution for many substrates at the same time.

In general, sensitivity of the system illustrated in FIG. 1 is proportional to the molecular weight of the substrate and Michaelis constant of the enzyme-substrate complex. Specifically, for the saccharase-sucrose system discussed, supra, the effective change in thickness of layer 12 on electrode 11 occurring between zero and full complexing is 0.1 Angstroms.

Although the foregoing description, for brevity, has been directed to only one form of specific reaction, namely that of an enzyme and substrate, the invention is also useful with other biological particles which specifically react. More particularly, the invention also contemplates use of a monomolecular layer of an antibody on the surface of electrode 11 in the apparatus of FIG. 1 and detection of cyclical changes of bonding of the complementary antigen to the antibody layer as an indication of the solution concentration of the complementary antigen. Similarly, the invention further contemplates use of a monomolecular layer of an antigen on the surface of electrode 11 in the apparatus of FIG. 1 and detection of cyclical changes of bonding of the complementary antibody to the antigen layer as an indication of the solution concentration of the complementary antibody. Both of these embodiments are possible because the interaction between the antibody and antigen species is sensitive to pH. In a typical instance, a pH of 3 will cause half-dissociation of the complex.

The foregoing describes a method and apparatus for detecting complexing of molecules in solution with surface-bound enzymes in an enzymatic reaction, and for optically measuring concentration of substrate in such reaction. A method and apparatus for optically measuring concentration of each of a plurality of substrates in a common solution reacting with each of a plurality of enzymes, respectively, in an enzymatic reaction, are also described.

While only certain preferred features of the invention have been shown by way of illustration, many modifications and changes will occur to those skilled in the art. It is, therefore, to be understood that the appended claims are intended to cover all such modifications and changes as fall within the true spirit of the invention.

We claim:

1. Apparatus for detecting complexing of substrate molecules with surface-bound enzyme molecules in an enzymatic reaction, comprising:
   a bath of said substrate molecules in solution;
   a first electrode coated with a monomolecular layer of said enzyme molecules and situated within said bath;
   a second electrode situated in said bath apart from said first electrode;
   means coupled across said electrodes for supplying thereto a D.C. potential with a superimposed sinusoidal voltage; and
   an ellipsometer analyzing polarized light reflected from said first electrode and producing an output signal having parameters dependent upon the nature of molecules on said first electrode.

2. The apparatus of claim 1 including phase sensitive detector means for producing a sensitive analysis of the output signal of said ellipsometer that is in phase with said sinusoidal voltage.

3. The apparatus of claim 1 wherein said means coupled across said electrodes for supplying thereto a D.C. potential comprises a slowly-varying D.C. voltage source and sine wave generating means connected in series.

4. The apparatus of claim 2 wherein said means coupled across said electrodes for supplying thereto a D.C. potential comprises a slowly-varying D.C. voltage source and sine wave voltage generating means connected in series, said apparatus further including means coupling the output of said sine wave voltage generating means to said phase sensitive detector means.

5. A method of detecting complexing of substrate molecules with surface-bound enzyme molecules in an enzymatic reaction comprising:
   immersing a first electrode coated with a monomolecular layer of said enzyme molecules in a bath of said substrate molecules in solution;
   immersing a second electrode in said bath spaced apart from said first electrode;
   applying a sinusoidally-varying potential impressed on a D.C. potential across said first and second electrodes; and
   sensing changes in amount of polarized light reflected from said first electrode to provide an indication of said complexing.

6. The method of claim 5 wherein the step of sensing changes in amount of polarized light reflected from said first electrode comprises determining only a voltage bearing a fixed phase relation to said sinusoidally-varying potential.

7. The method of claim 5 including the step of slowly varying pH of the solution in the vicinity of said first electrode.

8. The method of claim 7 wherein the step of slowly varying pH of the solution in the vicinity of said first electrode comprises slowly varying amplitude of said D.C. potential.

9. The method of claim 7 wherein the step of sensing changes in amount of polarized light reflected from said first electrode comprises determining only a voltage bearing a fixed phase relation to said sinusoidally-varying potential.

10. The method of claim 8 wherein the step of sensing changes in amount of polarized light reflected from said first electrode comprises determining only a voltage bearing a fixed phase relation to said sinusoidally-varying potential.

11. The method of claim 8 including the step of maintaining amplitude of said D.C. potential in excess of the amplitude range of said sinusoidally-varying potential.

12. The method of claim 11 wherein the step of sensing changes in amount of polarized light reflected from said first electrode comprises determining only a voltage bearing a fixed phase relation to said sinusoidally-varying potential.

13. Apparatus for determining concentration of biological particles of a first species, comprising:
   a bath of said particles in solution;
   a first electrode coated with a monomolecular layer of biological particles of a second species complementary to said particles of the first species;
   a second electrode situated in said bath apart from said first electrode;
   means coupled across said electrodes for supplying thereto a D.C. potential with a superimposed sinusoidal voltage; and an ellipsometer analyzing polarized light reflected from said first electrode and producing an output signal having parameters dependent upon the nature of molecules on said first electrode.

14. The apparatus of claim 13 wherein said biological particles of a first species comprise antibodies and said biological particles of a second species comprise antigens complementary to said antibodies.

15. The apparatus of claim 13 wherein said biological particles of a first species comprise antigens and said biological particles of a second species comprise antibodies complementary to said antigens.

* * * * *